United States Patent [19]
Burton et al.

[11] Patent Number: 5,449,250
[45] Date of Patent: Sep. 12, 1995

[54] METHOD FOR DISPOSING OF HAZARDOUS WASTES

[75] Inventors: Frederick G. Burton, West Richland; Dominic A. Cataldo, Kennewick; John F. Cline, Prosser; W. Eugene Skiens, Richland, all of Wash.

[73] Assignee: Battelle Memorial Institute, Richland, Wash.

[21] Appl. No.: 705,384

[22] Filed: May 23, 1991

Related U.S. Application Data

[60] Division of Ser. No. 555,113, Nov. 23, 1983, Pat. No. 5,116,414, which is a continuation-in-part of Ser. No. 314,809, Oct. 26, 1981, abandoned, and Ser. No. 314,820, Oct. 26, 1981, abandoned.

[51] Int. Cl.$^6$ ................................................. B09B 5/00
[52] U.S. Cl. .................................... 405/128; 588/250; 405/157
[58] Field of Search ............... 405/128, 129, 258, 157, 405/263; 588/249, 250, 259; 504/347

[56] References Cited

U.S. PATENT DOCUMENTS

| | | | |
|---|---|---|---|
| 4,453,857 | 6/1984 | Serra | 405/128 |
| 4,464,081 | 8/1984 | Hillier et al. | 405/128 |
| 4,988,236 | 1/1991 | Ramsey et al. | 405/157 |

*Primary Examiner*—David H. Corbin
*Attorney, Agent, or Firm*—Willian Brinks Hofer Gilson & Lione

[57] ABSTRACT

A method and system for long-term control of root growth without killing the plants bearing those roots involves incorporating a 2,6-dinitroaniline in a polymer and disposing the polymer in an area in which root control is desired. This results in controlled release of the substituted aniline herbicide over a period of many years. Herbicides of this class have the property of preventing root elongation without translocating into other parts of the plant. The herbicide may be encapsulated in the polymer or mixed with it. The polymer-herbicide mixture may be formed into pellets, sheets, pipe gaskets, pipes for carrying water, or various other forms. The invention may be applied to other protection of buried hazardous wastes, protection of underground pipes, prevention of root intrusion beneath slabs, the dwarfing of trees or shrubs and other applications. The preferred herbicide is 4-difluoromethyl-N,N-dipropyl-2,6-dinitro-aniline, commonly known as trifluralin.

19 Claims, 4 Drawing Sheets

FIG. 1
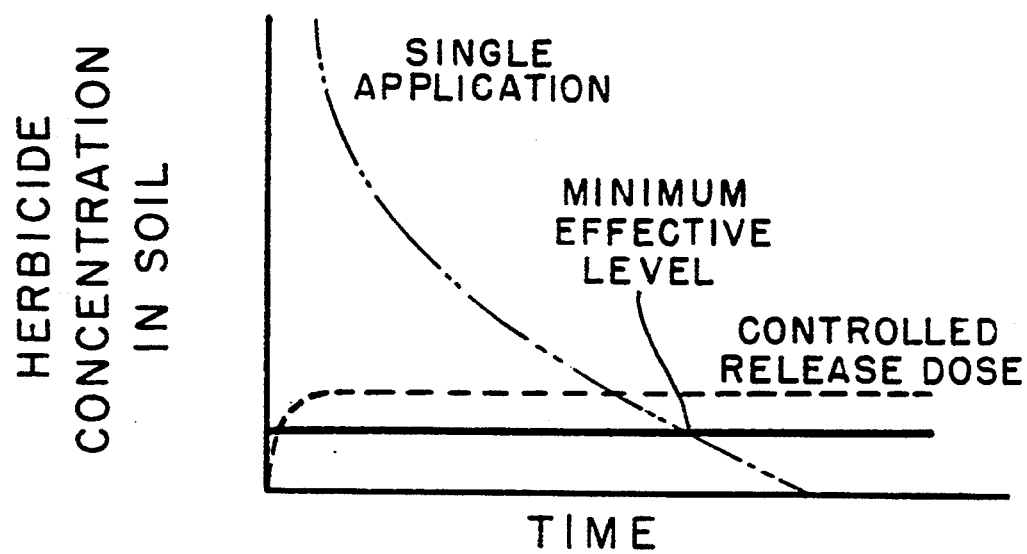
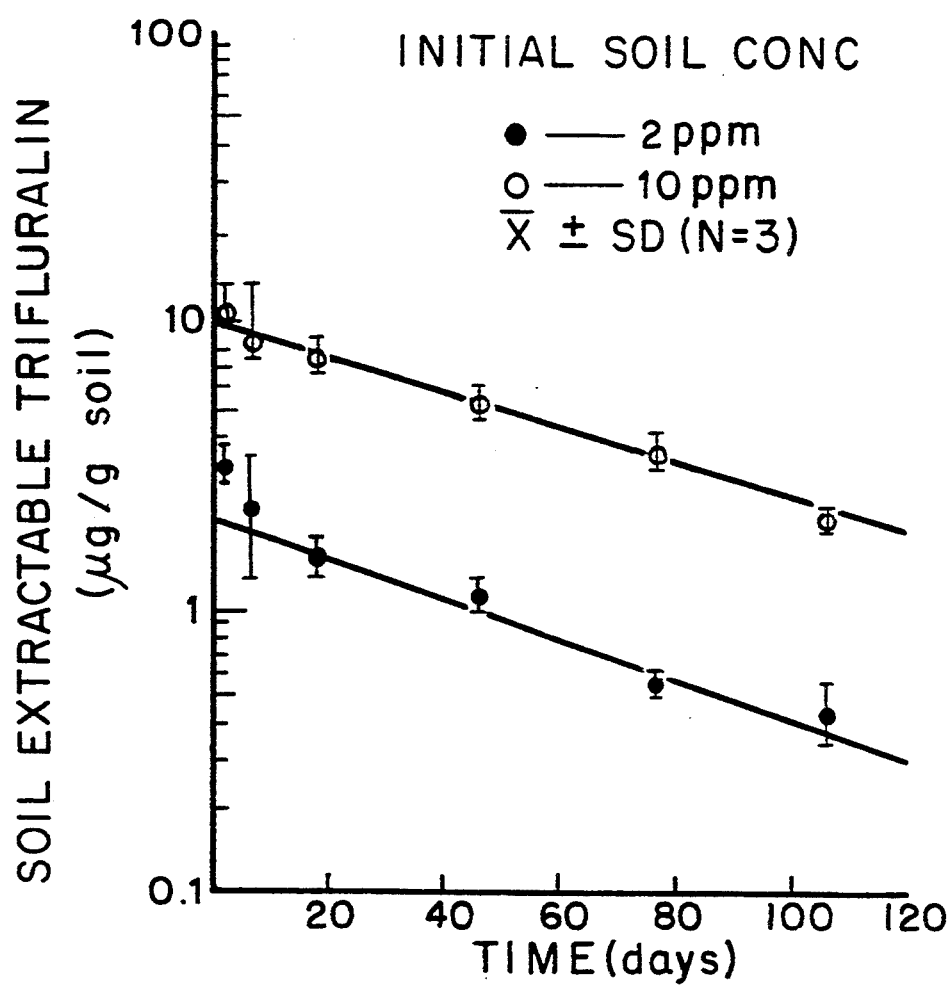
FIG. 2

METHOD FOR DISPOSING OF HAZARDOUS WASTES

This is a division, of application Ser. No. 06/555,1143, filed Nov. 23, 1983, now U.S. Pat. No. 5.116,414, now U.S. Pat. No. 5,116,414, which is a continuation-in-part of application Ser. No. 314,809 filed Oct. 26, 1981, abandoned and a continuation-in-part of application Ser. No. 314,810 filed Oct. 26, 1981 abandoned.

This invention is directed to the long-term control of root growth. There are a number of situations in which it is desirable to control the growth of the roots of a plant with out killing the plant. For example, low-level nuclear wastes and other solid wastes are frequently buried in the ground and vegetation is planted over them to minimize erosion and eliminate soil moisture. Roots of the plants may penetrate the wastes. Certain of the radioactive isotopes and other elements are taken up by the plants.

Uranium mill tailings present a still further problem. These tailings contain small amounts of uranium and radium-226, the latter being a decay product of uranium-238, which is the principal uranium isotope found in nature. Radium-226 in turn decays, forming various decay products, one of which is a radioactive gas, radon-222. The escape of radon is at present considered to be a primary health hazard connected with uranium mill tailings. Radon has been found to diffuse through the soil and escape. Because of its high molecular weight (which is the same as its atomic weight) radon-222 is much heavier than air and tends to accumulate in low places, for example, in the basement of houses.

One method which has been proven effective for retaining the radon is to cover the tailings with a layer of asphalt and then cover the asphalt with topsoil to prevent its deterioration by sunlight. To prevent erosion of the topsoil, it is desirable to plant vegetation over the asphalt. Instead of asphalt, very impervious clay has also been used. It has been found, however, that the roots of some plants tend to penetrate asphalt or clay, thus forming passages for the escape of radon. Moreover, the roots tend to take up other radioactive isotopes as described above in connection with the low-level nuclear wastes.

Another reason for restricting root growth without killing the plant is in connection with "dwarfing" of shrubs and trees. It has been the practice to accomplish this by grafting a desirable tree or shrub to a dwarf fruit stock, that is, one which produces a limited growth of roots. This has the effect of restricting the maximum growth of the tree or shrub. A more extreme example is in connection with the production of "bonsai" trees or shrubs. In this technique the tree or shrub is kept small by periodically digging it from the ground and pruning the roots. The growth of trees and shrubs under power lines presents a serious maintenance problem, since it has been necessary to periodically prune back the vegetation at a high expenditure of labor. It would be highly desirable, if it were practical, to restrict the growth of the vegetation so that frequent pruning is unnecessary.

Still another situation in which restriction of root growth is desirable, is in connection with buried water pipes, particularly sewers, septic tank dispersion fields, and drain fields for agricultural land. The usual treatment of such pipes may be called "post problem". It involves the boring out of the intruding roots by "power snakes" or the taking up of the pipes and physical removal of the offending roots. Sewage lines and septic tank dispersion fields present a particular problem because of the high nutrient quality of the water going through them. This increases the tendency of the roots to penetrate the pipe joints and to grow within the pipe. A similar problem sometimes exists with swimming pools or other below-ground containers of water. Furthermore, roots frequently grow beneath sidewalks, road pavements, patio or other slabs and cause damage. It is also desirable in some cases simply to prevent the spread of roots from one piece of property to another, for example, from trees into a neighbor's garden.

A somewhat different application involves the control of the direction of growth. For example, grape growers may desire deeper rooted grape plants. It would be advantageous to restrict the upward growth of their roots in order to encourage downward development.

There has been some prior attempt at chemical restriction of root growth. Otto Pauli of Farben Fabriken Bayer AG, Germany, has proposed (U.S. Pat. No. 3,231,398) utilizing, as a joint sealant in pipelines, asphalt containing a herbicide of the chlorophenoxy type, e.g., an ester of 2,4-dichlorophenoxy acetic acid, commonly known as 2,4-D. This is said to repel roots and prevent their contact with the asphalt. To the best of our knowledge, this has not gone into practical use. A difficulty with this approach is that these very potent herbicides tend to translocate within the plants and kill or seriously damage them.

There is, however, a group of compounds which behave differently in their action on plants although they fall within the general class of herbicides. These are the 2,6-dinitroanilines. When minute quantities of these compounds come in contact with plant roots they prevent further elongation by inhibiting cell division but do not translocate within the plant. For this reason, they are effective as preemergent herbicides for preventing the growth of unwanted weeds or grass in established crops. They prevent elongation of the roots coming from the seeds and so prevent the growth of plants from those seeds but do not translocate within and kill the established crops. (If applied in sufficiently large quantities, they may also kill mature plants be preventing root elongation). Compounds of this class are disclosed in a number of U.S. Pat. Nos. for example, Soper 3,111,403; Soper 3,257,190 and Lutz, et al. 4,101,582. A particularly well known example of these compounds is N,N-di-n-propyl-4-trifluoromethyl-2,6-dinitroaniline, which is known by the generic name trifluralin and is sold under the trademark, Treflan. It had occurred to us that these compounds might "repel" roots of growing plants to prevent their intrusion of wastes, pipes, or other undesirable locations or to restrict their growth to "dwarf" the plant. In connection with the burial of uranium tailings, we considered the direct incorporation of one of these compounds into the asphalt. We also considered the substitution of such compounds for the 2,4-D derivatives disclosed by Pauli in connection with pipe joints. This proved unsuccessful, however, since the asphalt apparently denatured or bound these herbicides and roots were not repelled.

SUMMARY OF THE INVENTION

This invention is directed to the restriction of the growth of roots of plants over a long period of time, up to about 100 years, without killing the plant or adversely affecting it (except for restricting its maximum growth) by placing an organic polymer incorporating a 2,6-dinitroaniline in the area in which root restriction is desired. We have found that the 2,6-dinitroaniline may be incorporated into polymers which are suitable for use in the form of pellets, sheets, strips, pipe gaskets, or pipes themselves. By incorporating them in polymers they can be made to release at such a rate that they will continue effective as root repellents for many years or decades while maintaining concentrations sufficiently low that the plants are not killed or injured.

Our method may be used in connection with buried waste or buried pipelines for preventing root intrusion, for preventing intrusion into swimming pools or basements or beneath sidewalks or other slabs, for preventing excess growth in right-of-ways, for the dwarfing of fruit trees or ornamentals, for controlling the direction of root propagation, or in fact any application in which restriction of root growth is desired, without killing the plants. It is effective over a period of many years or decades.

One method of employing the herbicide in combination with the polymer is to mix the dinitroaniline in the polymer and form the mixture into the pellets, sheets, etc., referred to above. Another method which is particularly applicable to the pellet form is to encapsulate the dinitroaniline in a polymer, that is, we may use a release system consisting of a tube or hollow cylinder with closed ends formed of the polymer and containing the dinitroaniline either pure or diluted by a suitable solvent.

BRIEF DESCRIPTION OF THE DRAWING

In the drawing,

FIG. 1 is a graph showing a generalized comparison of a single application of a herbicide with a controlled release system.

FIG. 2 is a graph showing the degradation of trifluralin in soil.

DETAILED DESCRIPTION

Figure 3:
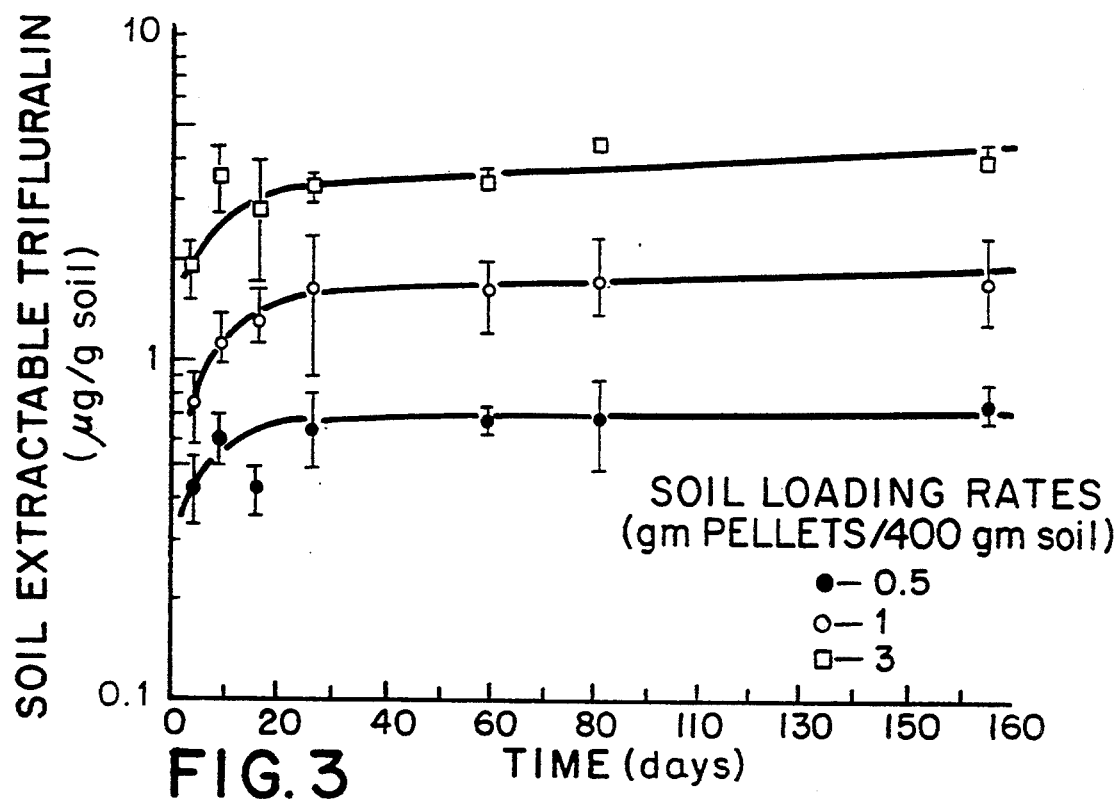
FIG. 3 is a graph showing the change in trifluralin concentration in soil with time utilizing our invention.

This invention is directed to a long-term control of root growth. There are a number of situations in which it is desirable to control the growth of the roots of a plant without killing the plant. For example, low-level nuclear wastes and other solid wastes are frequency buried in the ground and vegetation is planted over them to minimize erosion and eliminate soil moisture. Roots of the plants may penetrate the wastes. Certain of the radioactive isotopes and other elements are taken up by the plants.

Uranium mill tailings present a still further problem. These tailings contain small amounts of uranium and radium-225, the latter being a decay product of uranium-238, which is the principal uranium isotope found in nature. Radium-226 in turn decays, forming various decay products, one of which is a radioactive gas, radon-222. The escape of radon is at present considered to be a primary health hazard connected with uranium mill tailings. Radon has been found to diffuse through the soil and escape. Because of its high molecule weight (which is the same as its tends to accumulate in low places, for example, in the basement of houses.

A method and system for long-term control of root growth without killing the plants bearing those roots involves incorporating a 2,6-dinitroaniline in a root control is desired. The invention may be applied to protection of buried hazardous wastes. One method of disposing of hazrdous wastes in accordance with the present invention comprises placing said wastes in or on the ground, laying an impervious layer over said wastes, disposing over said layer a mixture of trifluralin and a polymer, covering said polymer with soil and planting vegetation in said soil. The mixture of polymer and trifluralin can be in the form of pellets and said pellets can be distributed over the impervious layer. The impervious layer can be an asphalt emulsion, or an impervious clay.

Another embodiment of the method of disposing of hazardous wastes in accordance with this invention comprises placing the hazardous wastes in or on the ground, disposing over these wastes a 2,6- dinitroaniline enclosed in a polymer, covering said polymer with soil and planting vegetation in said soil. The dinitroaniline can be mixed with the polymer. The mixture of polymer and dinitroaniline can be in the form of pellets and the pellets can be distributed over the wastes.

The invention will be described first in connection with the protection of uranium mill tailings. The tailings, either placed in an excavation or simply disposed on the surface of the ground, are first covered by a layer of a cationic asphalt emulsion which is allowed to harden. A few inches of soil are laid down and pellets of carbon-filled low-density polyethylene containing about 25 percent by weight trifluralin are distributed over the area. The pellets are about 9 millimeters in length and the same in diameter. The pellets are distributed at a rate of about 260 grams per square meter of surface. At least two feet of soil is then added and vegetation suitable to the climate is planted to prevent erosion. Instead of the asphalt, an impervious clay such as bentonite may be used.

Figure 8:
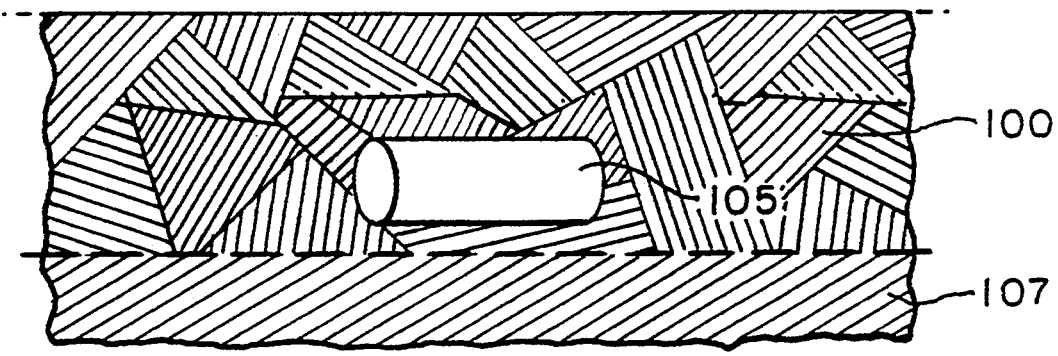
FIG. 8 depicts a controlled release device constructed in accordance with one embodiment of the present invention placed in a layer of soil above a layer of hazardous waste.
Figure 9:
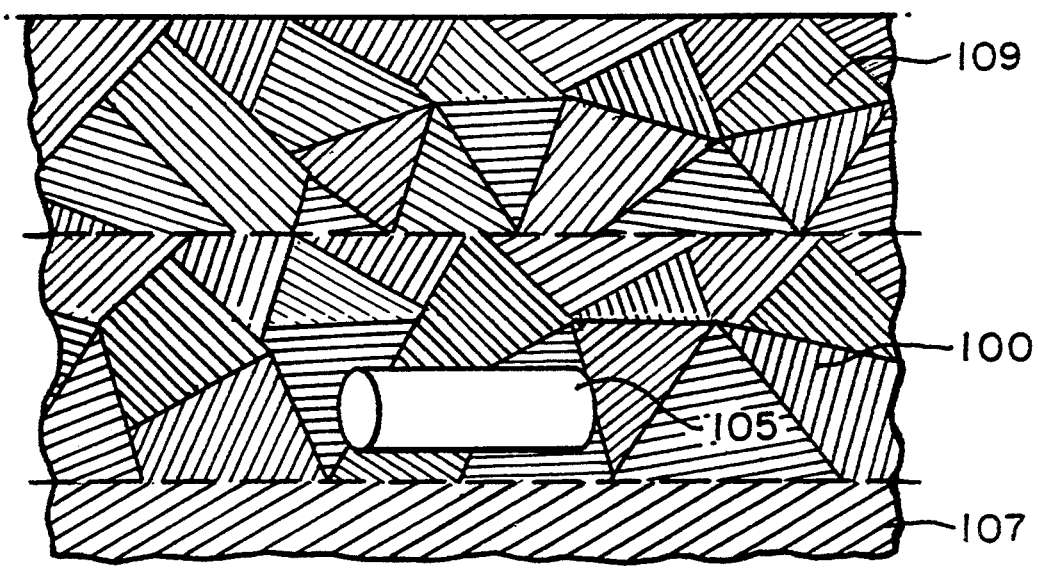
FIG. 9 depicts a controlled release device constructed in accordance with one embodiment of the present invention placed in a layer of soil beneath another layer of soil but above a layer of hazardous waste.
Figure 10:
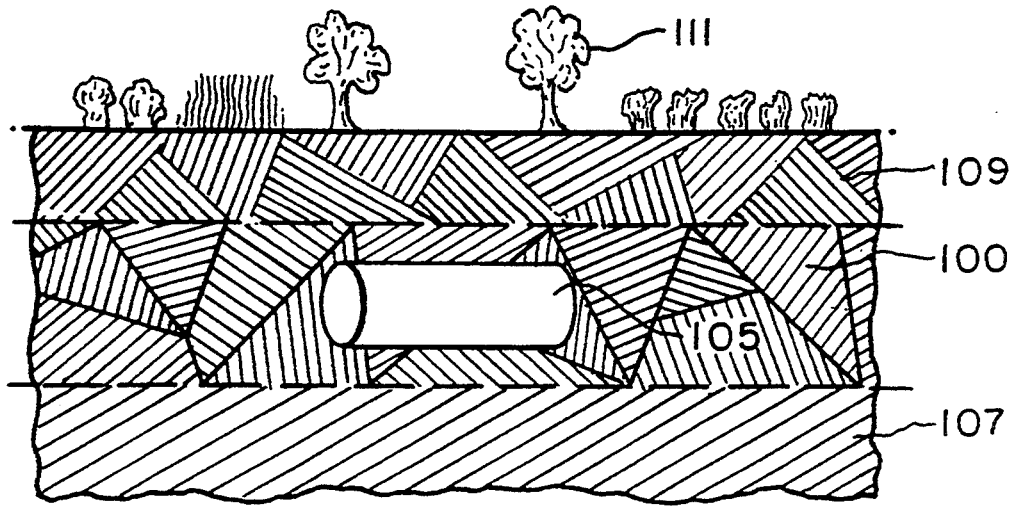
FIG. 10 depicts a controlled release device constructed in accordance with one embodiment of the present invention placed in a layer of soil beneath another layer of soil having vegetation planted therein and above a layer of hazardous waste.
Figure 11:
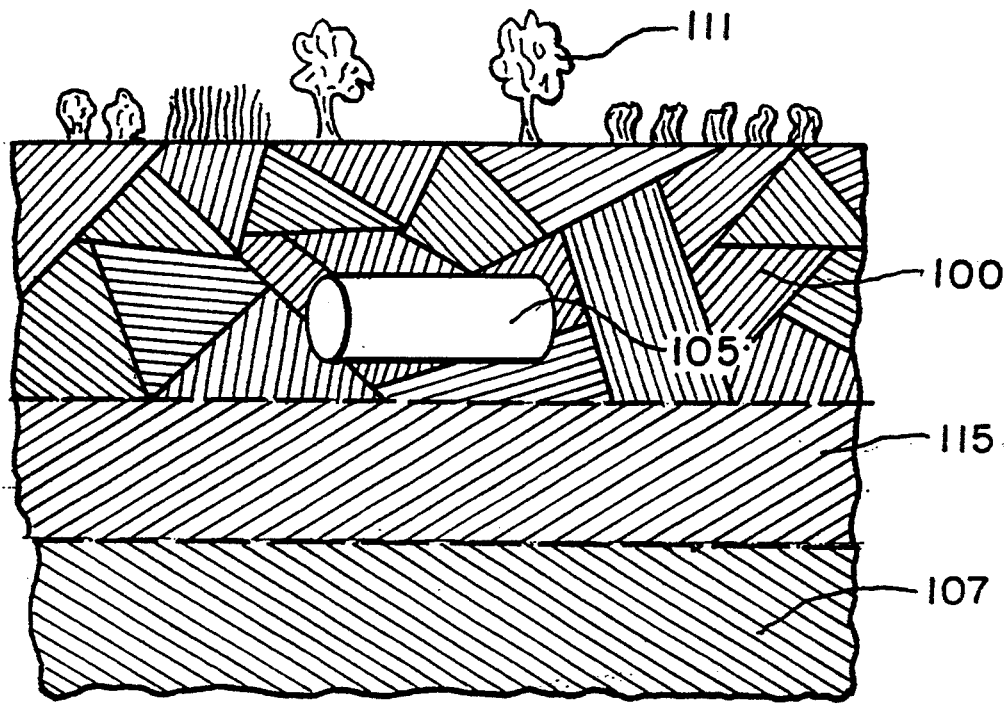
FIG. 11 depicts a controlled release device constructed in accordance with the present invention placed in a layer of soil that has vegetation planted therein, above a layer of clay which, in turn, in above a layer of clay in turn, is above a layer of hazardous waste.
Figure 12:
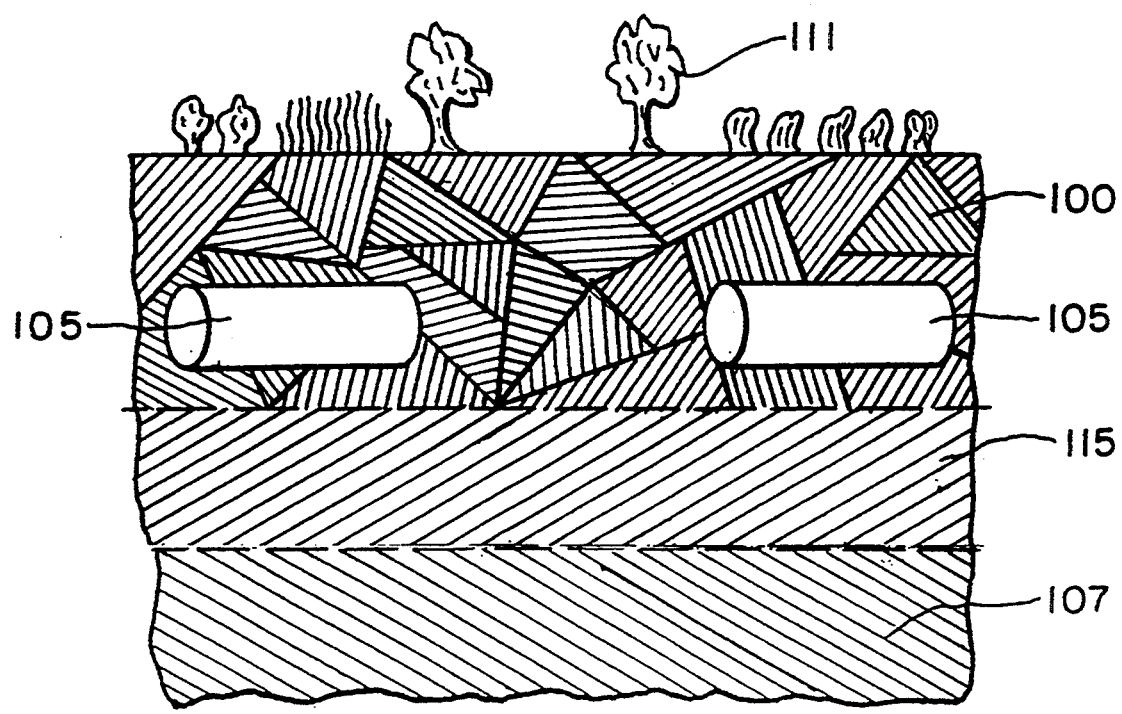
FIG. 12 depicts the same layers as FIG. 11 except that two controlled release devices are shown.

FIGS. 8–12 illustrates the placement of the control release devices constructed in accordance with the present invention in the soil. Referring now to FIG. 8, the controlled releases device 105 is placed in layer of soil 100 above a layer of hazardous waste 107. Similarly, the device 105 is placed in a layer of soil 100 shown in FIG. 9. However, in FIG. 9, another layer of soil 109 is placed above the layer of soil 100 that contains the controlled releases device 105. The layers and the device 105 in FIG. 10 are the same as in FIG. 9. However, in FIG. 10 the layer of soil 109 has growing therein vegetation 111. In FIG. 11, the controlled release device 105 is placed in a manner similar to that of FIG. 10 except that a layer 115 of asphalt emulsion is placed beneath the layer 100. In FIG. 12, the controlled release device 105 is placed in a manner similar to that of FIG. 11 except that the layer 120 is specifically an impervious clay. FIG. 12 is similar to FIG. 11. The difference is that FIG. 12 illustrates the use of two devices 105 in the soil layer 100.

EXPERIMENTAL BASIS

The experimental basis for this invention will now be described. Referring to the drawing, FIG. 1 provides a generalized comparison of the effect of a single application of herbicide to soil in the usual manner with the controlled release dose provided by our system. A single application of an herbicide such as trifluralin results in much higher concentrations than those necessary to achieve the desired effect. However, with time, the concentration of the herbicide will be reduced by physical, chemical and biological action to levels less than the minimum effective level (MEL). By using our system involving "Controlled Release Devices," the active ingredients can be maintained at levels above the MEL for extended periods of time.

In the following reports of experiments, herbicides tested are designated by the common names under which they were obtained commercially. The common names and a chemical name for each are as follows:

| Common Name | Chemical Name |
|---|---|
| Trifluralin | 4-trifluromethy-2,6 dinitro-N,N-dipropyl aniline. |
| Oryzalin | 4-sulfonamido-2,6 dinitro-N,N-dipropyl aniline. |
| Dinoseb (DNBP) | 2,4-dinitro-6-sec-butyl phenol. |
| Bromoxynil | 3,5-dibromo-4-hydroxybenzonitrile. |
| Paraquat | 1,1'-dimethyl-4,4'-bipyridinium dichloride. |
| Bromoxynil Octanoic Acid Ester | 3,5-dibromo-4-hydroxybenzonitrile, octanoic acid ester. |
| TBA | 2,3,6-trichlorobenzoic acid. |
| 2,4-D | 2,4-dichlorophenoxy acetic acid. |

Because of the importance of the two products oryzalin and trifluralin and to better show their relationship, their structural formulas are given as follows:

Oryzalin

4-sulfonamido-2,6-dinitro-N,N-dipropyl aniline

Trifluralin

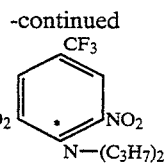

4-trifluoromethyl-2,6-dinitro-N,N-dipropyl aniline

EXAMPLE 1

Short-term Biobarrier Study

In our first experiment, we identified a suitable herbicide and tested its effectiveness in preventing plant roots from reaching buried waste. Fifteen lysimeters, 15 cm in diameter and 50 cm long, were made from Lucite ® (polyacrylate) tubing to allow observation of root growth. Ritzville loam soil was used (see Wildung, U.S. ERDA Report BNWL-2272 (1977) for a description of this soil type). The five herbicides listed in Table 1 were placed in a 1-cm thick layer of soil 30 cm below the soil surface, and each herbicide treatment was replicated three times. Herbicide was applied at the rate of 20 lb. of active ingredient per acre, considerably higher than that recommended for weed control. The soil was fertilized with ammonium sulfate at the rate of sixty pounds of available N per acre, irrigated to 20% soil moisture and seeded to Russian thistle (*Salsola kali* L.). Building paper was placed around the outside of the Lucite lysimeters to prevent light from affecting root growth, but growth and configuration of the roots could be observed by removing the paper cover. All lysimeters were placed in a growth chamber for 30 days.

During the subsequent harvest, the roots and above ground parts of the plants were photographed and then collected for yield determinations. Soil was removed from the roots by gentle running water; above ground parts were clipped at ground level. The roots and above ground parts were oven-dried at 60° C. for 48 hours before weights were taken.

The effectiveness of five herbicides as root carriers are shown in Table 1. The plants grew normally without visible effects to the roots and above ground parts in the control

TABLE 1

Results of Above Ground Parts and Roots of Russian Thistle Grown in Lysimeters Treated with Five Different Herbicides

| | Leaves and Stems | | Roots | |
|---|---|---|---|---|
| Herbicide | Effect | Oven Dry Wt. (g)* | Penetration | Oven Dry Wt. (g)* |
| Oryzalin | N. grn** | 21.1 ± 1.6 | Stopped at barrier | 9.2 ± 1.6 |
| Paraquat | N. grn | 25.7 ± 1.3 | Grew past barrier | 6.9 ± 0.4 |
| TBA | dead | 1.4 ± 0.3 | Not visible | 0.4 ± 0.1 |
| Dinoseb | N. grn | 9.9 ± 2.2 | Grew past barrier | 2.4 ± 0.4 |
| Trifluralin | N. grn | 23.9 ± 2.5 | Stopped at barrier | 10.4 ± 1.4 |
| Control | N. grn | 25.1 ± 3.7 | Throughout soil | 8.1 ± 0.9 |

*N = 3, X ± SE
**N. grn = normal green and in soils treated with oryzalin, paraquat, and trifluralin. The plants grew for a short time and died in the soil treated with TBA. Roots grew through the barriers of dinoseb, paraquat, and the control, and the dinoseb treated lysimeters produced less root and leaf biomass.

For these reasons, paraquat, TBA, and dinoseb were not considered as potential applicants as biobarriers where a vegetation cover is desired. Oryzalin and trifluralin treated barriers stopped elongation through the treated soil and were not harmful to the remaining plant parts. Though both herbicides were determined to be satisfactory root barriers, the less water-soluble trifluralin did not seem to move within the soil profile as much as oryzalin. zalin.

EXAMPLE 2

Intermediate-term Biobarrier Study

This study was designed to accomplish a sustained release of a selected herbicide from a synthetic, polymeric carrier/delivery system (PCD system). This delivery system acts as a reservoir for the herbicide, prevents excessive loss or degradation of the compound for a prolonged period, and regulates delivery of the compound at a suitable rate to prevent root growth through the polymer/herbicide zone.

Seven herbicides were selected for this study based on their mode of phytotoxic action and soil sorption behavior. This includes trifluralin, oryzalin, bromoxynil, dinoseb, paraquat, bromoxynil octanoic acid ester, and TBA. The herbicides were incorporated into silicone polymer sheets at 10% by weight. Control treatments consisted of sheets of silicone rubber without incorporated herbicide. The sheets were cut in a circular shape 13.7 cm in diameter to fit the lysimeter. A 2.5 cm diameter hole was placed in the center and two holes 1.25 cm in diameter placed adjacent to the center hole. Holes were used to determine if the herbicide would move beyond the sheet and effectively prevent root penetration through voids or breaks in normal sheet biobarriers.

The circular sheets were placed within the soil of a 50-cm long lysimeter made of lucite tubing 15 cm in diameter. The lysimeter contained a 15-cm bottom layer of soil, the treated or control polymer sheet, and an additional 35-cm layer of soil above the sheet. The soil was then fertilized with nitrogen and distilled water added to give a soil moisture content of 20%. To prevent light exposure to the root zone, building paper was wrapped around each lysimeter. The paper cover could be lifted from time to time to observe root growth.

The lysimeters were planted to Russian thistle and placed in a controlled environmental growth chamber with 16 hours light per day at temperature settings of 20° C. day and 12° C. night.

Plants were maintained for 50 days. During this time a photographic record was maintained of root development patterns with respect to barrier placement and changes in shoot morphology resulting from phytotoxicity of the soil-placed herbicides. At the termination of the experiment, shoot tissues were oven-dried and weighed. One lysimeter from each of the treatments was split longitudinally and the roots recovered by washing away the soil with running water. These were subsequently oven-dried and weighed to determine root distribution and phytotoxin effects.

The effects on root and shoot yields of various hericides impregnated into sheet-type PCD systems are shown in Table 2. Roots did not pass through the treated PCD system even though a 2.5-cm hole was placed in the middle of the sheet, but roots grew throughout the soil profile of the control. By contrast, when herbicide was added directly to the soil, roots did penetrate paraquat and dinoseb barriers. The reason for this is most likely due to replenishment of soil paraquat and dinoseb levels by the PCD system, while in the case of the directly amended soil, soil sorption and degradation rapidly decrease the herbicide concentrations below levels at which the roots may be controlled. Shoot and root yields were reduced in lysimeters containing dinoseb and bromoxynil. These plants were slow, growing through the season. Though shoot yields were greatly reduced in the paraquat, bromoxynil, bromoxynil acid ester, and TBA-treated PCD systems, root yields were nearly the same as in the trifluralin-and oryzalin-treated PCD systems. It was observed in PCD system treatments using paraquat, bromoxynil, bromoxynil octanoic acid ester and TBA that plants grew vigorously until the roots came in contact with the barrier resulting in the immediate death of upper plant parts. Higher root yields in the control probably resulted from growth throughout the entire soil profile since

TABLE 2

Leaf, Stem, and Root Weights (g/lysimeter) of Russian Thistle Plants Grown in Lysimeters with PCD Systems.

| Treatment | Shoot Yield (Leaf and Stem Tissue) | Root Yield |
| --- | --- | --- |
| Trifluralin | 6.43 ± 0.96 | 4.75 |
| Oryzalin | 5.44 ± 0.59 | 4.76 |
| Dinoseb | 1.36 ± 0.10 | 1.54 |
| Bromoxynil | 2.41 ± 1.75 | 0.53 |
| Paraquat | 1.68 ± 0.57 | 5.48 |
| Bromoxynil Octanoic Acid Ester | 1.68 ± 0.57 | 5.45 |
| TBA | 1.44 ± 0.24 | 3.77 |
| Control | 6.61 ± 0.55 | 9.15 | the roots were not restricted by the treatment with herbicides. These are preliminary studies; however, data indicate that trifluralin, and oryzalin were the most promising herbicides for use in future PCD systems.

The behavior of different plant species was investigated to determine the minimum effective levels of trifluralin sufficient to restrict basipetal root growth. We used 5-cm (ID)×35-cm lysimeters containing 1200 g Ritzville silt-loam (18% moisture). A 2-cm zone, located 25 cm from the surface, contained known concentrations of trifluralin. After the seeds were planted, 13 to 24 days elapsed before the roots ceased longitudinal growth due to the concentration of trifluralin in the soil surrounding the root tips. Minimum effective levels for individual plan species were determined by analysis of trifluralin in soil at the point at which root elongation ceased. These ranged from 0.3 ppm for Russian thistle (tumbleweed) to 6.4 ppm for crown vetch (Table 3).

Since it is essential that the chemical biobarrier be of

TABLE 3

Minimum Effective Levels of Trifluralin Required to Inhibit Longitudinal Root Growth, and Effects on Shoot and Root Dry Weight

| Plant | Time for Root to Reach Treated Zone[a] (days) | Duration of Study (days) | Minimal Effective Concentration[b] (ppm) | Effect on Shoot/Root Dry Weight[c] (% of Control) |
| --- | --- | --- | --- | --- |
| Russian Thistle | 17 | 31 | 0.3 | 92/82 |
| Tansy Mustard | 21 | 45 | 4.7 | 90/85 |
| Fourwing Saltbush | 15 | 45 | 4.0 | 72/77 |
| Gardner Saltbush | 16 | 45 | 3.1 | 115/94 |
| Winter Fat | 18 | 55 | 1.9 | 57/50 |
| Crown Vetch | 14 | 45 | 6.4 | 94/115 |
| Rocky Mtn. Penstemon | 24 | 45 | 0.9 | 99/101 |
| Whitmar Wheatgrass | 13 | 45 | 1.5 | 102/97 |
| Thickspike Wheatgrass | 21 | 59 | 0.7 | 71/67 |
| Russian Wildrye | 14 | 56 | 0.5 | 86/82 |
| Lewis Blue Flax | 13 | 56 | 2.5 | 83/101 |
| Bitterbush | 14 | 54 | 1.2 | 95/96 |

[a]Roots grew from 18 to 24 cm below surface; 2-cm treated zone located 25 cm from surface
[b]Plugs for analysis removed from soil just below root zone
[c]Mean of three replicates minimal toxicity, root and shoot dry-matter production was determined in our experiments. With the exception of winter fat and fourwing saltbush, trifluralin had little effect on dry-matter productions no symptoms of toxicity were observed. The weight reductions observed may have resulted from a substantial loss (40-60%) in rooting volume, caused by the presence of the trifluralin-loaded soil layer.

The saltbush was believed to be represetative of other dry-land shrubs such as sagebrush (*Artemisia tridentata*).

The latter was not suitable for experimental use because of its slow growth rate.

For the studies of controlled release of trifluralin from polymers, it was necessary to accurately determine the release rates of herbicide from the polymeric system. A continuous flow system has been used to measure the steady-state release rates of trifluralin from several types of polymers, and permitted us to make an evaluation of their suitability for use in the proposed application. Based on these results, as well as other parameters (physical characteristics, loading ability, and polymer cost), carbon-filled polyethylene and polypropylene polymers appear to be the best choices. These polymers combine low release rates (therefore long lifetimes for a given loading) with slow polymer degradation rates when in contact with soil, and relatively low cost to provide suitable reservoirs for the proposed application.

Among the different forms of these polymers, low density polyethylene is preferred. However, high density polyethylene and polypropylene are also suitable.

Table 4 shows the in vitro release rates determined by the experiments referred to above. The lower release rates are preferred.

TABLE 4

Release Rates (±SD) of Trifluralin from Polymeric Carrier Delivery Systems (sheets)

| Polymer Type | Release Rate μg/daycm² |
| --- | --- |
| Polyetherurethane | 3.4 ± 1.0 |
| Poly (ethylene-vinyl acetate) | 9.3 ± 3.3 |
| Silicone Rubber | 91.7 ± 16.8 |
| Polyester (aromatic) | 7.3 ± 1.7 |
| Polyethylene | 1.5 ± 0.2 |
| Polypropylene | 4.2 ± 0.4 |

We looked at two systems in which trifluralin was placed in tubing, the ends sealed, and the release rates determined.

The first of these was silicone tubing. A piece of tubing 4.65 mm OD×3.35 mm ID×28 mm long was plugged in one end with Medical Grade silicone rubber, filled with trifluralin crystals and a small amount of silicone oil, and the other end sealed with Silastic. The devices were run for approximately seven weeks, with an unacceptably high release rate, 124 μg/day/device±SD, about 16.5 μg/day/cm².

The second devices were fabricated from polyehylene tubing. The tubing was 4.83 mm OD×3.75 mm ID×23 mm long. It was heat sealed at one end, filled with trifluralin crystals and silicone oil, and then heat sealed at the other end. The release rate was 12.7 μg/day/device±4.3 SD, about 3.6 μg/day/cm².

The silicone oil was placed in the devices to increase the surface area available for the trifluralin to diffuse into. Triffluralin is quite soluble in the oil. The oil is too soluble in the silicone tubing. It rapidly penetrates the tubing and is lost. It does remain in the polyehylene tubing and is probably helpful in maintaining a constant release rate.

Deep placement of the PCD devices in soil should result in a loss of released trifluralin primarily by microbial decomposition and chemical degradation (hydrolysis). To maintain the MEL this loss must be compensated by an equivalent release of the herbicide from the PCD device. In our study, a Ritzville silt-loam amended with 20 or 10 ppm trifluralin, and maintained at 18% moisture, resulted in a calculated half-life of approximately 50 days for trifluralin (see FIG. 2 of the drawing). Although half-life will vary with soil class and field moisture conditions, this calculation provides an indication of the long-term, sustained, in-situ release rate of trifluralin required from a PCD system in order to maintain the MEL.

In the initial studies we used membranes due to the simplicity of the system; however, for practical adaption to many field studies, membranes may cause problems in application and use. Pellets are frequently a much more practical approach to accomplish the objective. In the first studies with pellets, we used 10% trifluralin-loaded polypropylene devices 2 to 3 nun in diameter and 5 to 7 mm long, with a release rate (determined in the continuous flow system) of 19.8 μg/day/g±2.4 SD. Release in soil indicated a somewhat lower rate than this flow-system-determined value, possibly indicating a reduced concentration gradient of the herbicide between the environment and the polymer under these conditions.

Polypropylene pellets such as are described above were distributed in soil in three different proportions (0.5, 1.0 and 3.0 g pellets per 400 g soil) and soil trifluralin concentrations were measured over a period of time. Results are shown in FIG. 3 of the drawing. In each case, near equilibrium conditions were reached within 30 days.

Based on the in vitro release rate and the amount of trifluralin in the pellet, these devices could last only 14 years (because of their small size) at zero-order release rate. However ever, taking into account the degradation rate of trifluralin and the equilibrium levels which were determined for these devices, it appears that the in situ release rate is approximately half the rate determined in vitro, possibly indicating a reduced concentration gradient of the herbicide between the environment and the polymer under field conditions. It is therefore possible that the potential lifetime of the devices in the field may be increased by a factor of approximately two.

Because of the theoretical lifetime of these devices was insufficient for the proposed application, where a 100 year useful life is desired, larger devices (9 mm in diameter and 9 mm long) were fabricated to take advantage of the extended release rate possible with these devices. Release rates after 70 days were on the order of 25 to 30 $\mu$g/day/device. This release rate (on a surface area basis) is actually somewhat higher than that of the smaller devices, possibly because these devices were molded (leading to randomly arranged polymer chains) while the smaller devices were extruded (leading to more-organized polymer chains).

These 9 mm$\times$9 mm pellets have also been used in studies to determine their suitability in preventing root penetration. A layer of soil was placed in a lysimeter, the pellets were added in densities from 1 to 4 in$^2$/pellet, the lysimeter was filled with soil and seeded with a test plant. At the end of the study, the lysimeters were taken apart and the density of pellets necessary to prevent root penetration was determined. Using barley as the test plant, roots ceased to elongate in the treatment zone at all densities tested.

Studies on these devices have been extended to determine the characteristics of trifluralin release under various conditions. Initial analyses indicate that the concentration of trifluralin recovered from the soil after diffusion from the device is inversely proportional to soil moisture content of between 6 and 18%. Diffused trifluralin is strongly sorbed by the soil (Ritzville silt-load), reaching a concentration of $\sim$2 ppm at 2 cm from the pellet after 30 days; at 8–10 cm from pellet, concentrations were undetectable. Similar results were obtained in wet soil having a high clay content.

In a later experiment, pellets 9 mm in diameter and 9 mm long, weighing about 0.7 g were molded from low density polyethylene having a melt index of 22, containing 30 pph (parts by weight per hundred of polyethylene) carbon black and 40 pph trifluralin. The carbon black serves to stabilize the polymer, increase the possible concentration of trifluralin in the polymer, and slow down its release rate, which was, after the initial burst 15–20 $\mu$g/day/pellet in vitro.

Based on the information cited, we have developed a trifluralin-releasing device with a theoretical lifetime approaching 100 years. Equilibrium concentrations of trifluralin in soil can be adjusted (along with the theoretical life of the device) to suit specific needs.

A second embodiment of our invention is in connection with buried pipes. We have found that the 2,6-dinitroanilines may be incorporated into polymers which are suitable for use in the form of gaskets, sheets, strips or pellets, or as the pipes themselves, and are released at rates such that root elongation is inhibited and root penetration of the pipe prevented.

When the pipe is impervious, so that root penetration occurs only at Joints, it is obviously most economical to incorporate the herbicide only in the gasket or otherwise place it only adjacent to the Joints. If, however, the pipe is perforated to permit seepage in or out, it may be desirable to incorporate it into the pipe material.

If the pipe Joints are intended to be sealed, the gasket should be of a resilient material. We consider butyl rubber, chlorobutyl rubber, natural rubber, EPDM (ethylene-propylened-dione monomer) rubber and silicone rubber to be satisfactory although other elastomers may be used if the Joints are not sealed, as in drain fields and sewage-dispersal fields, polyethylene and polypropylene may be used, either in the form of O-rings within the Joints or sheets wrapped around the exterior.

Where the pipe is perforated, it may be necessary or desirable to incorporate the herbicide directly into the pipe itself. Polyethylene, polypropylene and polyvinyl chloride (PVC) as well as the elastomers mentioned above, are suitable pipe materials which are also suitable for the incorporation of the herbicides. Alternatively, strips or sheets of polyethylene ethylene or polypropylene incorporating the herbicide may be wrapped around the perforated pipe, or pellets of the same composition may be spread over the pipe. The elastomers mentioned above may also be used in these manners.

As a retrofit expedient, rods, strips, or sheets incorporating a 2,6-dinitro aniline can be inserted on the inner surface of a pipe by a plumbers' snake or similar device. For example, expandable mesh or tubing can be pressed against the pipe by a coiled spring or similar element.

By proper selection of the polymer, the dinitroaniline and the proportions of each, the protection can be made effective for many years, e.g., up to 100 years.

Figure 4:
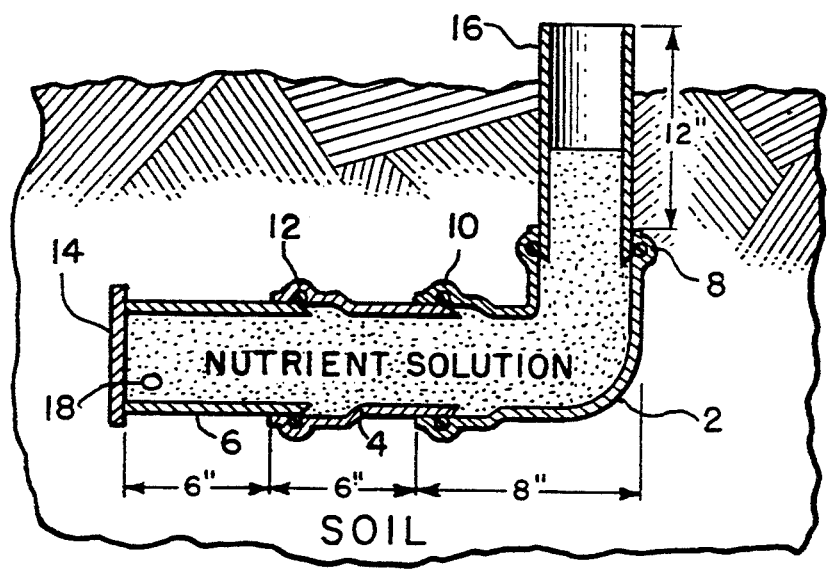
FIG. 4 is a vertical cross section of an experimental embodiment of our invention as applied to the protection of pipes against root intrusion.

In FIG. 4 we show the preferred embodiment of this application of our invention incorporated into the experimental setup. This employs synthetic rubber gaskets incorporating trifluralin.

A sewer line is shown including several sections: 2, 4, and 6. The Joints are sealed by gaskets 8, 10 and 12. These gaskets are formed of butyl rubber incorporating 40 pph of trifluralin, i.e., 40 parts by weight of trifluralin to 100 parts of butyl rubber.

For purposes of the experiments, which will be described later, one end of the pipe was closed by a seal 14, while the other end, 16 was open and extended above the ground. An aerator 18 supplied air to the nutrient solution in the pipe. Experimental examples leading up to the selection of this design and composition will now be described.

EXAMPLE 3

Our initial experiments involved the selection, formulation and in vitro testing of a number of elastomeric materials suitable for our test. The initial tests were carried out using an RTV silicone rubber. Although this material was easily formulated and proved the feasibility of the concept, silicone rubber is expensive, and had rather poor physical properties for use as an "O" ring compression seal. Therefore, we redirected our efforts to other materials more suitable for "O" ring applications. These included EPDM (ethylene-propylenediene monomer) rubber, chlorobutyl rubber and butyl rubber. These were formulated with either trifluralin or 2,4-D to provide the root intrusion barrier and other suitable compounding agents to provide strength and resilience, and cured to produce either sheets or pellets for subsequent in vitro and in situ testing to determine release rates, effectiveness, and effective life of the barrier. After preliminary testing, butyl rubber was selected for further studies. This material is commonly employed in the gaskets, possesses good physical properties as a seal when loaded with high concentrations of trifluralin, and exhibits suitable release rates.

In vitro release rates and effective lifetime were first determined. Tests included butyl rubber itself and a chlorobutyl rubber. The chlorobutyl rubber was formed in a sheet with a thin layer of pure chlorobutyl rubber sealed over the trifluralin-loaded chlorobutyl rubber (45 pph trifluralin i.e., 45 parts by weight trifluralin to 100 parts of the polymer) to give a diffusion layer of the same material for the trifluralin to diffuse through. Over a nine-week period the release rate of trifluralin was approximately constant, 13.4 micrograms per day per $cm^2 \pm 1.1$ SD. For this loading and release rate, provided the release rate did not change with time, one gram of the loaded chlorobutyl rubber behind one sq centimeter of surface would furnish sufficient trifluralin to release at this rate for 63 years. In actual fact, over an extended period of time, the diffusion rate would drop off making the actual useful lifetime nearer 200 years. For the proposed application this probably far exceeds the reasonable lifetime of the sewer pipe.

Release rates were also determined for a 14 pph addition of trifluralin to butyl rubber. The test pieces were in the form of a cylinder approximately one centimeter in diameter by 0.4 cm thick. The release rate was approximately constant for a four-week period starting eight weeks after the beginning of the flow testing 8.7 micrograms a day per $cm^2 \pm 1.2$ SD. For this loading and this rate, the test piece with one gram of butyl rubber behind the surface area of one sq centimeter would continue to release at this rate for 32 years. However, because of the decrease in release rate with time, the useful lifetime would probably be approximately 100 years.

EXAMPLE 4

These studies involved in situ soil studies and determination of intrusion effectiveness. They included determination of comparative release rates and effectiveness in inhibiting root growth when trifluralin or 2,4-D are contained in either butyl rubber or asphalt blends. Specific objectives were to evaluate (1) release rates of trifluralin and 2,4-D (acid form) contained in butyl rubber sewer pipe gasket material and its subsequent soil mobility; (2) release rates and soil mobility for trifluralin and 2,4-D blended in asphalt; (3) determination of the minimum effective levels of trifluralin and 2,4-D required to inhibit root elongation or penetration of the barrier; and (4) the comparative phytotoxicity and usefullness of trifluralin and 2,4-D. Since pipe blockage by willow roots is notoriously common, experiments were conducted using that plant.

All experiments were conducted using 5 cm (I.D.)×36 cm laboratory lysimeters containing 1200 grams Ritzville silt loam (pH 6.9) and transplanted willow cuttings to simulate deep placement of barriers and subsequent root interactions. Each lysimeter was implanted with 3 one-sq-centimeter butyl rubber devices containing 40 pph trifluralin at 26 cm below the soil surface. After 60 days, trifluralin concentrations in the soil averaged 8 ppm at 0 to 2 cm above the devices and decreased to 0.6 ppm at 4 to 6 cm above the devices. Asphalt blended with trifluralin at 5% by weight resulted in soil concentrations of 1.4 ppm at 0 to 2 cm and decreased to less than 0.05 ppm at 4 to 6 cm. Longitudinal root growth was inhibited by the trifluralin-containing butyl rubber devices but not by the trifluralin-asphalt blend. Extraction of the latter showed trifluralin to be extractable with methanol but apparently bound, preventing subsequent diffusion to the soil.

The well known herbicide 2,4-D was tested in butyl rubber devices at 5.6 and 40 pph and in asphalt at 5% by weight. No discernible diffusion pattern such as that noted with triflutalin was observed in this case, because the 2,4-D is much more volatile and moves through the soil profile more rapidly. Soil concentrations ranged from less than 1 to 2.5 ppm over the entire soil column whether the herbicide was supplied in butyl rubber or as a blend with asphalt. In no case did the willow seedlings survive beyond 32 days of growth in the presence of 2,4-D. Unfortunately, due to time and funding limitations, no quantitative measure of root and shoot growth over the term of the experiment could be obtained in the lysimeters treated with trifluralin. However, root intrusion beyond the soil-implanted devices was prevented without detrimental effects to the plant by the butyl rubber-trifluralin device but not by the asphalt-trifluralin blend, the butyl rubber-2,4-D, or asphalt-2,4-D implant. In all 2,4-D treatments, the willow seedlings yellowed and died.

EXAMPLE 5

Greenhouse/field simulation of root intrusion devices.

The most common location where plant roots enter an operating sewer line is at the pipe joints which employ gaskets as seals. A greenhouse study was undertaken to compare the effectiveness of the protection systems using 2,4-D and trifluralin-impregnated seals as methods to prevent plant root intrusions of sewer lines.

Lengths of sewer pipe including one joint were placed vertically into a soil profile within a 2×2×3 ft plant growth container (FIG. 4). The joint was placed approximately 18 in. below the soil surface with six different types of seals (Table 5): (1) A perfect O-ring treated with triflutalin was placed in one point, sealing the joint to water flow; (2) a trifluralin-treated O-ring with holes drilled into it large enough to permit nutrient solution to leak slowly out and for roots to pass inwardly; (3) a perfect untreated O-ring; (4) an untreated O-ring with drilled holes so plant roots could penetrate the seal and nutrient solution could leak slowly out; (5) a seal made by mixing 18 g 2,4-D with 342 g of asphalt cement which was pressed into the pipe joint; and (6) a seal made by mixing 18 g trifluralin with 324 g asphalt cement and pressing the mixture into the pipe joint. The test pipes were filled to the joints with aerated nutrient solution to increase the probability of the roots entering the pipes through any opening in the seal to obtain nutrients and water (FIG. 4).

Two experimental pipes were placed in each of the four growth containers as shown. Soil was then placed around the pipes, planted with weeping willow seedlings and irrigated.

After about 3 months, the sewer pipes were removed from the boxes that were located in the greenhouse. Before the pipes were removed, the willow limb lengths were measured. The soil was removed from around the pipe and the root contact was observed. Pictures were taken of the above-ground plant parts and the roots' relationship to the treated pipe seals. The following results were observed and are shown in Table 6. The limbs and roots of the plants grown in the box containing the 2,4-D-treated seal were dead. The limb lengths were 41±12 cm. The roots were very small and dead and were located in the upper 6 to 8 inches of the soil profile. The soil moisture was at near field capacity, showing the plants had

TABLE 5

Treatments for Field Simulation of Root Intrusion Devices

| Treatment No. | Treatment | Box No. |
|---|---|---|
| 1 | Good O-ring — trifluralin treated | 1 |
| 2 | Holed O-ring — trifluralin treated | 1 |
| 3 | Good O-ring — no treatment-control | 2 |
| 4 | Holed O-ring — no treatment (no trifluralin) | 2 |
| 5 | Asphalt seal — impregnated with 2,4-D | 3 |
| 6 | Asphalt seal — impregnated with trifluralin | 3 |

TABLE 6

Status of Willow Plants in Boxes at Completion of Study

| Treatment of Pipe Seal | Limb and Root Viability | Average Limb Length (cm)* | Soil Moisture Content |
|---|---|---|---|
| Box 1, Trifluralin | live | 130 ± 12 | dry |
| Box 2, Control | live | 114 ± 14 | dry |
| Box 3, 2,4-D | dead | 41 ± 12 | wet |

*X ± SD transpired only limited amounts of water. The limbs and roots of the plants grown in the boxes containing the control seals and trifluralin-treated seals were alive and growing at harvest time. The limb lengths were 114±14 cm and 130±12 cm, respectively, and the roots were growing throughout the soil profiles of both boxes. Nearly all of the available soil moisture had been removed from the entire soil profile in both boxes showing that the plants were transpiring. No differences in plant growth were observed between the control and trifluralin treated boxes. No toxic effects from trifluralin were observed, contrary to the case of the 2,4-D asphalt treatment.

The root contact with the pipe near the treated seals were as follows: No roots grew near the pipe containing the 2,4-D/asphalt seals, and the entire plant was finally killed. However, the roots grew near the pipe but did not enter the pipe Joints containing the trifluralin treated 0-rings. In the control containing an untreated holed 0-ring the roots grew along the pipe and into the Joint, so visual differences were observed between the vegetative growth in the trifluralin treated and control boxes.

Figure 5:
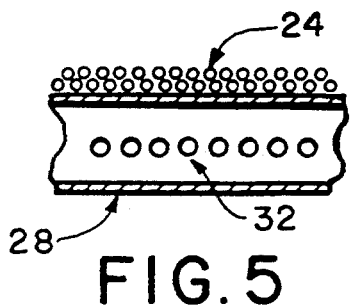
FIG. 5 shows diagrammatically an embodiment involving the use of pellets in connection with pipe protection.
Figure 6:
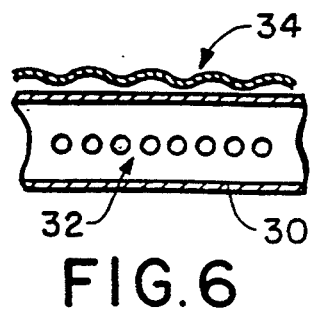
FIG. 6 shows diagrammatically an embodiment employing a plastic sheet in connection with pipe protection.
Figure 7:
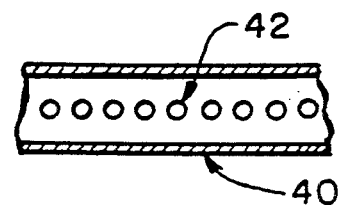
FIG. 7 shows diagrammtically a perforated plastic pipe.

In FIG. 5 we show a buried pipe 28 having perforations 32. Over it are spread trifluralin-containing polymeric pellets 24. FIG. 6 shows a pipe 30 having perforations 32. Over it is placed a trifluralin-containing polymeric sheet. FIG. 7 shows a pipe 40 made of a polymer mixed with trifluralin and having perforations 42.

While we have disclosed specific embodiments of the invention in considerable detail, it will be apparent to those persons skilled in the art that various changes can be made. For example, while we have performed experiments only with trifluralin and oryzalin among the dinitroanilines, the property of limiting root growth without translocating is common to that group of compounds, so numerous ones may be substituted.

We, therefore, wish our invention to be limited solely by the scope of the appended claims.

We claim:

1. A method for disposing of hazardous wastes comprising the following steps:
    (a) placing a first layer of soil above said wastes; and
    (b) placing at least one controlled release device in said first layer of soil, said device comprising a polymer containing a herbicidal 2,6-dinitroaniline distributed throughout said polymer, said 2,6-dinitroaniline releasing out of said device into said first layer of soil at a sufficiently fast rate to maintain the concentration in said layer high enough to prevent roots of plants from inducing into said layer, but low enough to avoid killing said plants.

2. The method of claim 1 further comprising the step of placing a second layer of soil above said first layer of soil.

3. The method of claim 1 further comprising placing said waste in the ground prior to step (a).

4. The method of claim 3 further comprising planting vegetation in said second layer of soil.

5. The method of claim 4 further comprising the following steps prior to placing said first layer of soil:
    covering said waste with a third layer of soil, then;
    covering said third layer of soil with cationic asphalt emulsion; and
    allowing said emulsion to harden.

6. The method of claim 4 further comprising the following steps prior to placing said first layer of soil:
    covering said waste with a third layer of soil; then,
    covering said third layer of soil with impervious clay.

7. The method of claim 4 further comprising the following steps prior to placing said first layer of soil:
    covering said waste with a third layer of soil; then,
    covering said third layer of soil with bentonite.

8. The method of claim 4 wherein a plurality of controlled release devices are placed in said first layer, said devices being in the form of pellets and said pellets being spaced close enough apart to maintain the concentration of 2,6-dinitroaniline sufficiently high to prevent the roots of plants from intruding from said second layer through said first layer but sufficiently low to avoid killing said plants.

9. The method of claim 1 wherein the 2,6-dinitroaniline is trifluralin.

10. The method of claim 4 wherein the 2,6-dinitroaniline is trifluralin

11. The method of claim 8 wherein the 2,6-dinitroaniline is trifluralin.

12. The method of claim 7 wherein the amount of trifluralin in said device is sufficiently large to prevent roots of plants from growing through said layer for up to 63 years.

13. The method of claim 12 wherein said at least one controlled release device comprises 2,6-dinitroaniline incorporated into a plastic sheet.

14. The method of claim 1 wherein said polymer is selected from the group consisting of: trifluralin and oryzalin.

15. The method of claim 1 wherein said 2,6-dinitroaniline is selected from the group consisting of a polymer selected from the group consisting of: polyetherurethane, poly (ethylene-vinyl acetate), silicone rubber, aromatic polyester, polyethylene, polypropylene, butyl rubber, chlorobutyl rubber, natural rubber, ethylene-propylene-diene monomer rubber and polyvinyl chloride.

16. The method of claim 1 wherein said hazardous waste comprises radioactive waste.

17. A method for disposing of hazardous waste comprising the following steps:
    (a) placing said waste in soil;
    (b) placing at least one controlled release device in said soil, said device comprising a polymer containing a herbicidal 2,6-dubutroaniline distributed throughout said polymer;
    (c) allowing herbicidal 2,6-dinitroaniline to release into the soil at a sufficiently fast rate to maintain the concentration in said soil in a zone around said waste high enough to prevent roots of plants from introducing into said zone but low enough to avoid killing said plants.

18. The method of claim 17 wherein the step of placing said waste comprises
    digging a ditch;
    disposing of the waste into said ditch; and,
    covering said waste-containing ditch with a layer of soil.

19. A method for disposing of nuclear waste comprising the following steps:
    (a) placing nuclear waste in a defined area;
    (b) covering the defined area with soil; and,
    (c) placing a controlled release device in said soil said device comprising a polymer containing a herbicidal 2,6-dinitroaniline distributed throughout said polymer;
    (d) allowing herbicidal composition to release into the soil at a sufficiently fast rate to maintain the concentration in said soil in a zone around said waste high enough to prevent roots of plants from introducing into said zone but low enough to avoid killing said plants.

* * * * *